US008529448B2

(12) United States Patent
McNair

(10) Patent No.: US 8,529,448 B2
(45) Date of Patent: Sep. 10, 2013

(54) COMPUTERIZED SYSTEMS AND METHODS FOR STABILITY—THEORETIC PREDICTION AND PREVENTION OF FALLS

(75) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 320 days.

(21) Appl. No.: 12/982,631

(22) Filed: Dec. 30, 2010

(65) Prior Publication Data

US 2011/0190593 A1 Aug. 4, 2011

Related U.S. Application Data

(60) Provisional application No. 61/291,657, filed on Dec. 31, 2009.

(51) Int. Cl.
*A61B 5/00* (2006.01)
(52) U.S. Cl.
USPC .......................................... 600/301; 600/300
(58) Field of Classification Search
USPC .................................................. 600/300–301
See application file for complete search history.

(56) References Cited

U.S. PATENT DOCUMENTS

| 6,835,176 | B2 | 12/2004 | McNair | |
| 6,997,882 | B1 * | 2/2006 | Parker et al. | 600/534 |
| 7,258,667 | B2 | 8/2007 | McNair | |
| 7,423,537 | B2 * | 9/2008 | Bonnet et al. | 340/573.1 |
| 7,479,890 | B2 * | 1/2009 | Lehrman et al. | 340/573.1 |
| 2001/0004234 | A1 * | 6/2001 | Petelenz et al. | 340/539 |
| 2004/0236235 | A1 * | 11/2004 | Fujita et al. | 600/500 |

(Continued)

OTHER PUBLICATIONS

Alzayer L, et al. The accuracy of individual Berg Balance Scale items compared with the total Berg score for classifying people with chronic stroke according to fall history. J Neurol Phys Ther. 2009;33:136-43.

(Continued)

*Primary Examiner* — Bill Thomson
*Assistant Examiner* — Bobby Soriano
(74) *Attorney, Agent, or Firm* — Shook, Hardy & Bacon LLP

(57) ABSTRACT

A system, methods and computer-readable media are provided for the automatic identification of patients according to near-term risk of sudden kinematic injury (falling). Embodiments of the invention are directed to event prediction, risk stratification, and optimization of the assessment, communication, and decision-making to prevent falling in humans, and in one embodiment take the form of a platform for wearable, mobile, untethered monitoring devices with embedded decision support. Thus the aim of embodiments of the present invention relates to automatically identifying persons who are at risk for falls through the use of an inexpensive, noninvasive, portable, wearable electronic device and sensors equipped with signal-processing software and statistical predictive algorithms that calculate stability-theoretic measures derived from the digital accelerometer and gyroscope timeseries acquired by the device. The measurements and predictive algorithms embedded within the device provide for unsupervised use in the home or in general acute-care and chronic-care venues and afford a degree of robustness against variations in individual anatomy and sensor placement. In some embodiments, the present invention provides a leading indicator of near-term future abnormalities, proactively alerting the user, for example, 2 hours or more in advance, and providing the wearer and/or care providers with sufficient advance notice to enable effective preventive maneuvers to be undertaken. In one exemplary embodiment, the device is equipped with radiofrequency telecommunication capabilities that enable integration with case-management software, electronic health record decision-support systems, and consumer personal health record systems.

20 Claims, 6 Drawing Sheets

(56) References Cited

U.S. PATENT DOCUMENTS

| | | | |
|---|---|---|---|
| 2005/0182305 A1* | 8/2005 | Hendrich | 600/300 |
| 2005/0240086 A1* | 10/2005 | Akay | 600/300 |
| 2007/0027369 A1* | 2/2007 | Pagnacco et al. | 600/301 |
| 2007/0197881 A1* | 8/2007 | Wolf et al. | 600/300 |
| 2008/0009686 A1* | 1/2008 | Hendrich | 600/301 |
| 2008/0045804 A1* | 2/2008 | Williams | 600/300 |
| 2008/0081958 A1* | 4/2008 | Denison et al. | 600/300 |
| 2009/0318779 A1* | 12/2009 | Tran | 600/301 |
| 2010/0261980 A1* | 10/2010 | Peng et al. | 600/301 |
| 2010/0261982 A1* | 10/2010 | Noury et al. | 600/301 |
| 2010/0286490 A1* | 11/2010 | Koverzin | 600/301 |

OTHER PUBLICATIONS

American Geriatrics Society, British Geriatrics Society, and American Academy of Orthopaedic Surgeons Panel on Falls Prevention. Guideline for the prevention of falls in older persons. J Am Geriatr Soc. 2001;49:664-72.

Austin N, et al. Fear of falling in older women: a longitudinal study of incidence, persistence, and predictors. J Am Geriatr Soc. 2007;55:1598-1603.

Beauchamp M, et al. Impairments in balance discriminate fallers from non-fallers in COPD. Respir Med. 2009;103:1885-91.

Berg K, et al. Clinical and laboratory measures of postural balance in an elderly population. Arch Phys Med Rehabil. 1992;73:1073-80.

Blum L, Korner-Bitensky N. Usefulness of the Berg Balance Scale in stroke rehabilitation: a systematic review. Phys Ther. 2008;88:559-66.

Boissy P, et al. User-based motion sensing and fuzzy logic for automated fall detection in older adults. Telemed J E Health. 2007;13:683-93.

Brauer S, et al. A prospective study of laboratory and clinical measures of postural stability to predict community-dwelling fallers. J Gerontol A Biol Sci Med Sci. 2000;55:M469-76.

Buatois S, et al. Posturography and risk of recurrent falls in healthy non-institutionalized persons aged over 65. Gerontology. 2006;52:345-52.

Chesi G, et al. Homogeneous Lyapunov functions for systems with structured uncertainties. Automatica 2003;39:1027-35.

Chong R, et al. Age-related changes in the center of mass velocity control during walking. Neurosci Lett. 2009;458:23-7.

Currie L. Fall and injury prevention. Annu Rev Nurs Res. 2006;24:39-74.

Dempsey J. Falls prevention revisited: a call for a new approach. J Clin Res. 2004;13:479-85.

Englander F, et al. Economic dimensions of slip and fall injuries. J Forensic Sci. 1996;41:733-46.

Fischer I, et al. Patterns and predictors of inpatient falls and fall-related injuries in a large academic hospital. Infect Control Hosp Epidemiol. 2005;26:822-7.

Freedson P, et al. Calibration of accelerometer output for children. Med Sci Sports Exerc. 2005;37(11 Suppl):S523-30.

Ganz D, et al. Will my patient fall? JAMA 2007;297:77-86.

Gietzelt M, et al. A clinical study to assess fall risk using a single waist accelerometer. Inform Health Soc Care. 2009;34:181-8.

Gillespie L, et al. Interventions for preventing falls in elderly people. Cochr Database Syst Rev. 1997;CD000340.

Goldberger A, West B. Applications of nonlinear dynamics to clinical cardiology. Ann New York Acad Sci. 1987;504:155-212.

Granata K, Lockhart T. Dynamic stability differences in fall-prone and healthy adults. J Electromyogr Kinesiol. 2008;18:172-8.

Haddad W, Chellaboina V. Nonlinear Dynamical Systems and Conrol: A Lyapunov-Based Approach. Princeton Univ, 2008; pp. 1-948. (Hard Cover Book being mailed on Jul. 6, 2011).

Haumschild J, et al. Clinical and economic outcomes of a fall-focused pharmaceutical intervention program. Am J Health Sys Pharm. 2003;60:1029-32.

Helbostad J, et al. Physical fatigue afects gait characteristics in older persons. J Gerontol A Biol Sci Med Sci. 2007;62:1010-5.

Hendriks M, et al. Lack of effectiveness of a multidisciplinary fall-prevention program in elderly people at risk: a randomized, controlled trial. J Am Geriatr Soc. 2008;56:1390-7.

Holbein-Jenny MA, et al. Balance in personal care home residents: a comparison of the Berg Balance Scale, the Multi-Directional Reach Test, and the Activities-Specific Balance Confidence Scale. J Geriatr Phys Ther. 2005;28:48-53.

Institute for Healthcare Improvement. Reducing harm from falls. Guidance document, 2008. Available at www.ihi.org/IHI/Topics/PatientSafety/ReducingHarmfromFalls/.

Kangas M, et al. Comparison of low-complexity fall detection algorithms for body-attached accelerometers. Gait Posture. 2008;28:285-91.

Kanten D, et al. Falls: an examination of three reporting methods in nursing homes. J. Am Geriat. Soc. 1993;41:662-6.

Karamanidis K, Arampatzis A, Mademli L. Age-related deficit in dynamic stability control after forward falls is affected by muscle strength and tendon stiffness. J Electromyogr Kinesiol. 2008;18:980-9.

Kim BJ, Robinson CJ. Ergonomics. Postural control and detection of slip/fall initiation in the elderly population. 2005;48:1065-85.

Kojima S, et al. Kinematics of the compensatory step by the trailing leg following an unexpected forward slip while walking. J Physiol Anthropol. 2008;27:309-15.

Lakshmikantham V, et al. Vector Lyapunov Functions and Stability Analysis of Nonlinear Systems. Kluwer, 1991; pp. 1-172 "This reference is available to the PTO and may be found in an IDS submitted on Jun. 8, 2011 for U.S. Appl. No. 12/982,625, filed Dec. 30, 2010."

Lajoie Y, Gallagher S. Predicting falls within the elderly community: comparison of postural sway, reaction time, the Berg balance scale and the Activities-specific Balance Confidence (ABC) scale for comparing fallers and non-fallers. Arch Gerontol Geriatr. 2004;38:11-26.

Lee J, Stokic D. Risk factors for falls during inpatient rehabilitation. Am J Phys Med Rehab. 2008;87:341-50.

Maeda N, et al. Predicting the probability for fall incidence in stroke patients using the Berg Balance Scale. J Int Med Res. 2009;37:697-704.

Marigold D, et al. Role of the unperturbed limb and arms in the reactive recovery response to an unexpected slip during locomotion. J Neurophysiol. 2003;89:1727-37.

Mathiyakom W, McNitt-Gray J. Regulation of angular impulse during fall recovery. J Rehab Res Dev 2008; 45:1237-48.

Muir S, et al. Use of the Berg Balance Scale for predicting multiple falls in community-dwelling elderly people: a prospective study. Phys Ther. 2008;88:449-59. a Lyapunov stability classifier. Dec. 28, 2004.

Narayanan M, et al. Longitudinal falls risk estimation using triaxial accelerometry. IEEE Trans Biomed Eng. Sep. 29, 2009. [Epub ahead of print].

Oliver D. Falls risk-prediction tools for hospital inpatients: Time to put them to bed? Age Ageing 2008;37:248-50.

Opalek J, et al. Wheelchair falls: 5 years of data from a level I trauma center. J Trauma Nurs. 2009;16:98-102.

Podsiadlo D, Richardson S. The timed "Up & Go": a test of basic functional mobility for frail elderly persons. J Am Geriatr Soc. 1991;39:142-8.

de Queiroz M, et al. Lyapunov-Based Control of Mechanical Systems. Birkhauser, 2000; pp. 1-316. "This reference is available to the PTO and may be found in an IDS submitted on Jun. 8, 2011 for U.S. Appl. No. 12/982,625, filed Dec. 30, 2010."

Reelick M, et al. The influence of fear of falling on gait and balance in older people. Age Ageing. 2009;38:435-40.

Ribeiro A, Pereira J. Balance improvement and reduction of likelihood of falls in older women after Cawthome and Cooksey exercises. Braz J Otorhinolaryngol. 2005;71:38-46.

Rizzo J, et al. Health care utilization and costs in a Medicare population by fall status. Med Care. 1998;36:1174-88.

Sattin R, et al. The incidence of fall injury ekents among the elderly in a defined population. Am J Epidemiol. 1990;131:1028-37.

Saverino A, et al. Falls in a rehabilitation setting: functional independence and fall risk. Eura Medicophys. 2006;42:179-84.

Tang P, Woollacott M. Inefficient postural responses to unexpected slips during walking in older adults. J Gerontol A Biol Sci Med Sci. 1998;53:M471-80.

Vassallo M, et al. Fall risk-assessment tools compared with clinical judgment: an evaluation in a rehabilitation ward. Age Ageing. 2008;37:277-81.

Vu M, et al. Falls in the nursing home: are they preventable? J Am Med Directors Assoc. 2006;7(3 Suppl):S53-8.

Scott V, et al. Multifactorial and functional mobility assessment tools for fall risk among older adults in community, home-support, long-term and acute care settings. Age Ageing. 2007;36:130-9.

* cited by examiner

COMPUTERIZED SYSTEMS AND METHODS FOR STABILITY—THEORETIC PREDICTION AND PREVENTION OF FALLS

CROSS-REFERENCE TO RELATED APPLICATIONS

This Application claims the benefit of priority of U.S. Provisional Application No. 61/291,657, filed Dec. 31, 2009, which is expressly incorporated by reference herein in its entirety.

BACKGROUND

Among people over the age of 65 years, fall-related injuries are the leading cause of death from injury. Forty percent of hospital admissions among people over the age of 65 years are reported to be the result of fall-related injuries, resulting in an average length of stay of 11.6 days. Each year, an estimated one third of older adults fall, and the likelihood of falling increases substantially with advancing age. The average medical cost of a fall is more than $20,000, and the total cost of falls is expected to reach $32.4 billion in 2020.

In 2005, a total of 15,802 persons over 65 years died as a result of injuries from falls. However, the number of older adults who fall and who sustain only minor or moderate injuries and seek treatment in clinics or physician offices is unknown. To estimate the percentage of older adults who fell during the preceding 3 months, the CDC has analyzed data from the 2006 Behavioral Risk Factor Surveillance System (BRFSS) survey. The results of that analysis indicated that approximately 5.8 million persons aged 65 years or older, or 15.9% of all U.S. adults in that age group, fell at least once during the preceding 3 months, and 1.8 million (31.3%) of those who fell sustained an injury that resulted in a doctor visit or restricted activity for at least 1 day. The percentages of women and men who fell during the preceding 3 months were similar (16.4% versus 15.2%, respectively), but women reported significantly more fall-related injuries than men (35.7% versus 24.6%, respectively).

Procedural prevention programs attempting to reduce the incidence of falls have to-date had mixed effectiveness, in part because the preventive measures address only a subset of the antecedent factors that lead to falls and in part because they place almost all of the burden of falls-prevention upon personnel other than the person who is at risk of falling and making the faller a passive non-participant. In that connection, a motivation for some embodiments of the invention is that, were non-demented people whose near-term risks of falling are elevated or increasing notified of that risk, many of those fallers would respond to such notifications by proactively self-initiating preventive measures, including temporarily refraining from transfers or other risky movements and contacting caregivers for help. Psychologically, this is far preferable to patient passivity and reactive responses by caregivers, insofar as persons at risk of falling not only fear falls; they also fear loss of independence and freedom. They do not like being disenfranchised in decisions about their own care, and they do not adhere to prevention programs that "medicalize" their situation and displace control to other authorities, including caregivers.

Falling is associated with common chronic diseases, such as Alzheimer's or other forms of dementia; peripheral neuropathies associated with diabetes or other conditions; Parkinson's disease; tremor; extrapyramidal dyskinesias that may be associated with psychiatric medications; cerebrovascular accident or transient ischemic attacks; cardiac problems including cardiac arrhythmias; diminished visual acuity; muscle weakness; lower-extremity joint replacements; and other conditions. However, while the absence of such conditions does reduce fall risk to a degree, it does not exclude the possibility of falling. It is for this reason that so much effort has been expended over the past 30 years on developing predictive models, such as the Berg Balance Scale, the Timed [Get]-Up-and-Go Test, and other metrics.

Mechanisms and types of falling have been the subject of several studies. Slips account for a high percentage of falls and subsequent injuries in community-dwelling older adults but not in young adults. This phenomenon suggests that although active and healthy older adults preserve a mobility level comparable to that of young adults, these older adults may have difficulty generating efficient reactive postural responses when they slip. This study tested the hypothesis that active and healthy older adults use a less effective reactive balance strategy than young adults when experiencing an unexpected forward slip occurring at heel strike during walking. This less effective balance strategy would be manifested by slower and smaller postural responses, altered temporal and spatial organization of the postural responses, and greater upper trunk instability after the slip. Kinematic data were collected from the right (perturbed) side of the body. Although the predominant postural muscles and the activation sequence of these muscles were similar between the two age groups, the postural responses of older adults were of longer onset latencies, smaller magnitudes, and longer burst durations compared to young adults. Older adults also showed a longer coactivation duration for the ankle, knee, and trunk agonist/antagonist pairs on the perturbed side and for the knee agonist/antagonist pair on the nonperturbed side. Behaviorally, older adults became less stable after the slips. This was manifested by a higher incidence of being tripped (21 trials in older vs. 5 trials in young adults) and a greater trunk hyperextension with respect to young adults. Large arm elevation was frequently used by older adults to assist in maintaining trunk stability. In an attempt to quickly reestablish the base of support after the slips, older adults had an earlier contralateral foot strike and shortened stride length. Thus the combination of slower onset and smaller magnitude of postural responses to slips in older adults may result in an inefficient balance strategy. Older adults needed secondary compensatory adjustments, including alengthened response duration and the use of the arms, to fully regain balance and prevent a fall. The shorter stride length and earlier contralateral foot strike following the slip indicate use of a more conservative balance strategy in older adults.

Typical stability assessments characterize performance in standing balance despite the fact that most falls occur during dynamic activities such as walking. The objective of one study was to identify dynamic stability differences between fall-prone elderly individuals, healthy age-matched adults, and young adults. Three-dimensional video-motion analysis kinematic data were recorded for 35 contiguous steps while subjects walked on a treadmill at three speeds. From this data, we estimated the vector from the center-of-mass to the center of pressure at each foot-strike. Dynamic stability of walking was computed by methods of Poincare analyses of these vectors. Results revealed that the fall-prone group demonstrated poorer dynamic stability than the healthy elderly and young adult groups. Stability was not influenced by walking velocity, indicating that group differences in walking speed could not fully explain the differences in stability. This pilot study supports the need for future investigations using larger population samples to study fall-prone individuals using nonlinear dynamic analyses of movement kinematics.

Maintaining balance and postural stability while performing functional activities is critical to an individual's independence and quality of life. When individuals are unable to maintain their total-body center of mass (COM) within the base of support, a loss of balance may result, leading to a fall. Effective interaction between the environment and the neuromuscular and musculoskeletal systems allows an individual to generate the ground reaction forces relative to the COM necessary for maintaining and recovering balance during expected and unexpected situations. The swing and support legs have a role in regulating angular impulse during fall recovery and the balance recovery strategies used by younger adults and older adult nonfallers and fallers is different. The multijoint dynamics and neuromuscular control used during fall recovery at the total-body, joint, and muscle levels are relevant aspects that are considered. Understanding the fall recovery mechanisms successfully used by younger and older adults allows us to begin to identify effective intervention strategies that target specific populations.

It is because of these factors that an improved predictive-preventive method and system would be valuable, and in embodiments of such methods and systems, prediction classification or decision-support alert signals emitted by the system are provided at logistically convenient times far enough in advance of a fall's occurrence to allow for effective preventive intervention in a majority of cases. Moreover, embodiments of such a method and system should be inexpensive and suitable for a much larger population who are at moderate risk of falls. Such a system would find use as a tool not only for surveillance and triaging the general medical-surgical patients in hospitals and other acute-care venues but also for ambulatory, free-living individuals such as athletes and the general elderly population who have one or more risk-factors for falls.

Effective fall preventive interventions vary, and optimal selection and personalized tailoring of them will depend upon the patient's context, gender, age, medications, neurological conditions such as Parkinsonism, history of previous falls, and other factors. In the case of a previously asymptomatic ambulatory person, effective preventive interventions may include consultation with the personal physician or nurse or physiotherapist, or presentation at a nearby outpatient department for diagnostic assessment and monitoring. In the case of a person with existing, known neurological conditions, effective preventive interventions may include admission to hospital for observation and neurological exams, provision of visiting nurse services, placement in an assisted-living or other long-term care facility, consideration for adjustment of medication regimen, or other alternatives.

Conventional pressure- and proximity- and accelerometry-based monitoring apparatus has been shown to have inadequate statistical sensitivity and specificity for the purpose of predicting falls.

When measurements rely upon motion patterns as the trigger or sentinel event for predicting incipient falling, the predictions are generally only relevant when the person is ambulating. Additionally, the advance notice provided by disturbed respiratory pattern signals is so short (milliseconds to seconds) as to preclude effective interventions to prevent the predicted falling occurrences. For example, the Bed-Ex™ Patient Occupancy Monitoring System and Motion Knowledge System's FallSaver™ and other 'proximity mat' and 'pressure mat' monitors for bed or chair surfaces have been used to detect and remotely signal unattended patient ambulation or [attempted] transfer-in-progress, and thereby predict patient falls. However, these often do not give a warning or alarm far enough in advance to enable nurses or other caregivers to reach the patient in time to assist them and prevent the fall.

Many prior art methods involve cumbersome, complex, expensive and/or invasive instrumentation, or require a skilled operator in attendance.

The most accurate predictive methods, such as multi-axis accelerometry, are expensive, are not widely available, are only performable by subspecialty-trained providers, and are only applicable to a small subset of patients who are already known to be at risk of falling based on other attributes.

The methods involve expensive measurements, such as genomic or proteomic laboratory tests that are not widely available and that have a performance turnaround time of many hours or days before the results and prediction are available for use, such that the prediction or classification is not timely with respect to interventions aimed at preventing the predicted occurrences.

The methods are sensitive to, and may be compromised or entirely confounded by, individual variations in patient anatomy and activities, such as transfers from chairs or wheelchairs or beds, transfers with slide-boards or grab-bars other prosthetics, patient movement and positioning, diurnal variations, etc.

The methods are sensitive to, and may be compromised or entirely confounded by, individual variations in operator positioning of proximity or pressure or accelerometer sensors on the patient's body or variations in the timing and method of acquiring the specimens or data that will enter into the prediction and classification.

A major deficiency of prior art is false-negative error rate and the absence of immunity to differences in daily activities and behavior mix. A further deficiency is activity-specificity, for example, the ability to detect or predict forward-falling while walking but not backward-falling and not falling while climbing stairs or running. Stride length decreases with advancing age, and a further deficiency of prior art is a restricted range of applicability in terms of gait and stride length.

Still a further deficiency is that existing systems do not take into account diurnal variations in persons' capabilities. For example, Parkinsonian patients tend to have greater stability deficits early and late in the day, and lesser deficits in the middle of the day. Whereas, some embodiments of the invention are sensitive to time-varying patterns in fall-risk.

Still a further deficiency is that some existing systems make or rely on assumptions about the cognitive status of the subject, this despite the fact that dementia and other cognitive and psychological factors clearly affect the precautions or lack thereof that are taken by fallers.

Still a further deficiency is that existing systems are unable to account for orthostatic hypotension, visual acuity, medication use, basic or instrumental activities of daily living, and other factors.

Still a further deficiency is that existing systems do not account for rotational acceleration, this despite the fact that various recovery movements that interrupt falls involve rotation of the torso and despite the fact that some types of falling involve rotations. Accelerometers are primarily able to measure 3-axis 3-degree-of-freedom acceleration in 3-D Cartesian coordinates. And, while it is theoretically possible to impute rotations (pitch, roll, yaw) from 2 or more 3-axis accelerometers, the angular precision and accuracy of doing so is presently inferior to the precision and accuracy of measuring rotations with a digital gyroscope.

Still a further deficiency of existing systems is that calibration and periodic recalibration of accelerometer output in V/m/sec2 in all three dimensions (which may be expensive and time-consuming) are required for accuracy. In contrast, some embodiments of methods and systems of the invention produce accurate predictions that are insensitive to accelerometer offset and drift; that require only infrequent checks to be sure that all three axes of acceleration detection are still functional; that permit the outputs in the measured 3 axes to diverge considerably from each other in gain or scale so long as each one is itself maintains approximately linear response; and that use 'relative' instead of 'absolute' acceleration readings, and thereby offer a distinct advantage in terms of ease-of-use and long-term cost-of-ownership.

Still further, no mathematical or biomechanical models have to-date appeared that are able to predict falling from a wheelchair or other prosthetic devices that are prevalent in rehabilitation or long-term care venues.

Moreover, an important consideration for widespread acceptability of a system and method for fall prediction and prevention is that the apparatus not unduly stigmatize the subject. The elderly staunchly protect their independence and resist most measures taken to protect them that might have a second-effect or indirect consequence of alerting their caregivers to diminished capability, causing the caregivers to reactively restrict the person's autonomy.

The necessity of moving an elderly person to a nursing home often is revealed by evidence denoting the risks attendant to allowing the person to remain at home. The fear of being placed in a nursing home is sufficiently strong for many that they will aggressively hide evidence or obfuscate occurrences of falling that may lead caregivers or authorities to take the decision to place them in a nursing home.

However, an apparatus that reinforces the autonomy of the wearer—enabling the wearer to accurately recognize and predict risks or trends in risks and self-initiate appropriate mitigations, refraining from motions or types of activity while the elevated risk is present, thereby preventing occurrences of falling—would be welcomed. The adverse outcomes would be prevented, and the wearer would remain independent and in control of their activities for a longer period of time than typically would otherwise happen. They would not be distressed in connection with autonomy-preserving cover-ups and obfuscation.

None of the prior art has examined mathematical stability properties of the measured variables, however; nor has the prior art made use of continuous realtime measurements over long periods of many hours. Despite the existence of pressure and proximity and accelerometer monitor type recording equipment for approximately 20 years, the analysis of long-timeseries data is traditionally restricted to abnormal patterns denoting falls' occurrence, and calculation and study of antecedent timeseries patterns, and other parameters are never performed. Only small selected portions of the recorded data are subjected to detailed analysis, and the rest are discarded unexamined or ignored.

SUMMARY

A system, methods and computer-readable media are provided for the automatic classification of patients according to near-term risk of unstable ambulation and transfers and resulting risk of falling. Embodiments of the invention are directed to event prediction, risk stratification, and optimization of the assessment, communication, and decision-making to prevent falls in humans.

For at least the reasons outlined above, embodiments of the present invention aim to alert the wearer to significant changes in stability at least some minutes in advance of markedly increased likelihood of falling, so that the person has adequate time to cease performing whatever detected pattern(s) of motions has (have) led to the predicted increase in fall risk. In some embodiments, when the case of upward or downward dose-titration of medications that are associated with fall risk, the signal denoting changed risk of falls may be sensed over a period of hours or days, not minutes.

Compared to traditional techniques, some embodiments of invention allow automatic processing of continuously acquired digital gyroscopic and accelerometer measurement of angular velocity in 3 axes (pitch, roll, yaw) and acceleration in 3 axes (X, Y, Z) and quantitative prediction of fall risk based on stability metrics derived from one or a plurality of motion parameters. Moreover, in comparison with manual methods, automated method-embodiments offer advantages in terms of absolute repeatability of measurements, immunity from errors related to observer fatigue, lapses of attention, and transcription, as well as efficiency and cost considerations that permit either more extensive and rigorous testing for the same cost as manual methods, or more rapid testing at lower cost.

In embodiments, a method for automatically predicting ventricular arrhythmias in an individual that are likely to result in sudden kinematic death (falling) is provided. The method includes the step of obtaining motion signals representative of electrical activity of the heart of an individual. The method also includes the steps of detecting the presence of instability of motion dispersion or other measurements in the signals, and determining, utilizing an objective function, a motion dispersion stability index (MdSI) from the signals, and determining the difference between the index and a reference value to detect the presence of instability of motion interval dispersion or other measurements in said signals, wherein a significant difference is indicative of an increased risk of said individual of falling. In one embodiment, the objective function comprises a timeseries calculated from serially-acquired waveform data embodying a Lyapunov exponent of one or a plurality of motion or other physiologic variables as functions of time. In one embodiment, the method further includes providing a notification when an increased risk for falling is determined. In some embodiments, this notification may be communicated to a health care provider and/or may be communicated to the individual by means of an audible alarm, text message, or phone call.

BRIEF DESCRIPTION OF THE DRAWINGS

The present invention is described in detail below with reference to the attached drawing figures, wherein.

DETAILED DESCRIPTION

Figure 1A:
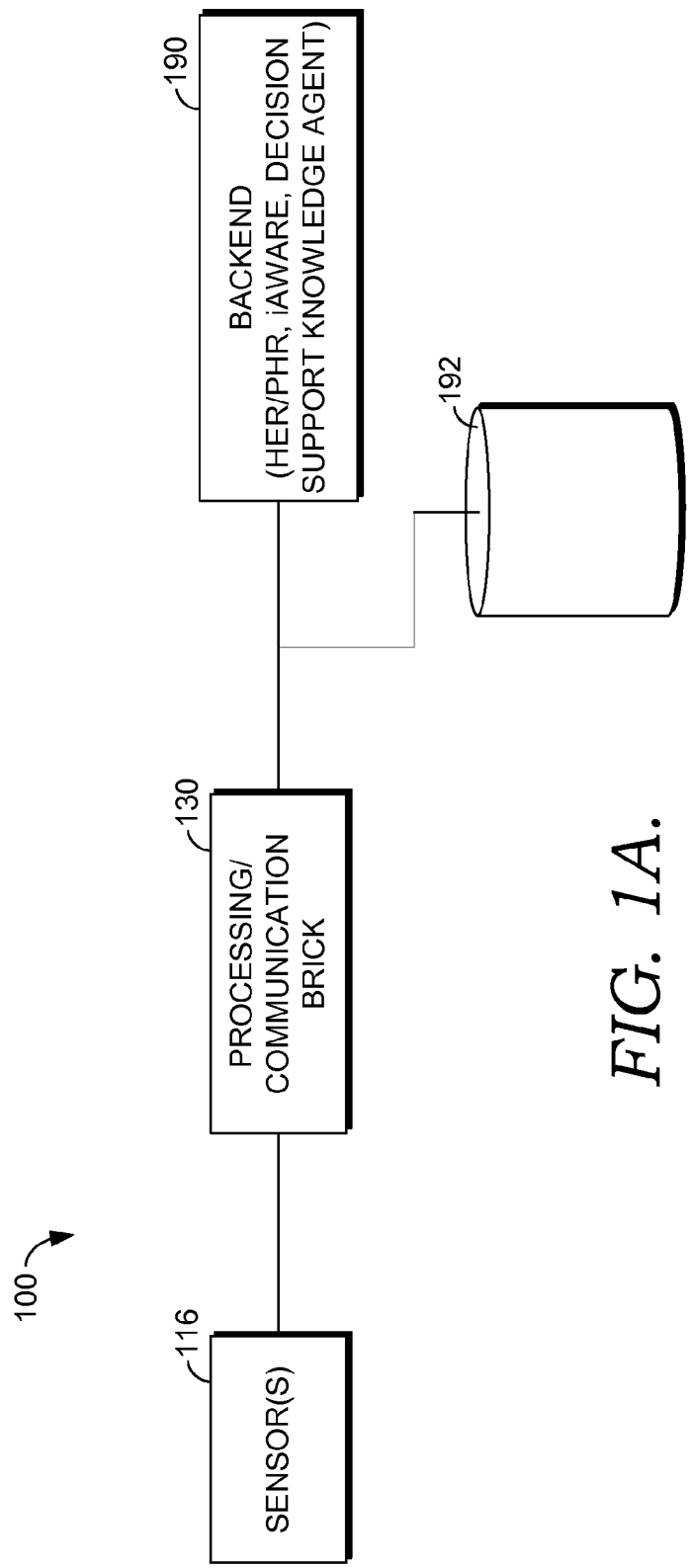
FIG. 1A depicts aspects of an illustrative operating environment suitable for practicing an embodiment of the invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable and nonremovable media, and contemplates media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

Embodiments of the present invention provide a computerized system, methods, and computer-readable media for automatically identifying persons who are at risk for falling through the use of a system, which in one embodiment, includes noninvasive, portable, wearable electronic device and sensors equipped with signal-processing software and statistical predictive algorithms that calculate stability-theoretic measures, such as a translational and rotational motion dispersion stability index (MdSI) for the individual, derived from a digital kinematic-signal timeseries acquired by the device. The measurements and predictive algorithms embedded within the device provide for unsupervised use in the home or in general acute-care and chronic-care venues and afford a degree of robustness against variations in individual anatomy and sensor placement. In embodiments, the present invention provides a leading indicator of near-term future abnormalities, proactively alerting the user (for example, 2 hours or more in advance, in one embodiment) and providing the wearer and/or care providers with sufficient advance notice to enable effective preventive maneuvers to be undertaken. In one exemplary embodiment, the device is equipped with radiofrequency telecommunication capabilities that enable integration with case-management software, electronic health record decision-support systems, and consumer personal health record systems.

By way of example and not limitation, a user using an embodiment of the invention may be able to go about his or her daily routine but be provided an advanced warning of any abnormalities such as a detonation or improvement of the user's condition or an increased likelihood of an event such as falling, Sudden Cardiac Death (SCD) COPD, asthema, TIA, stroke, or other conditions, for example. In one embodiment, the user may don one or more sensors capable of acquiring gyroscopic or accelerometer measurement, or both, of angular velocity and acceleration, which could be a chest-strap sensor, a badge sensor attached to or integrated into the user's clothing, a watch-sensor or other sensor in approximate contact with the user and that is wirelessly communicatively-coupled to a smart phone located on or near the user's body. In this exemplary embodiment, the smart-phone may include an app which when executed receives user data from the sensors, calculates the stability-theoretic measures, and communicates the results with the user, the user's health care provider, case-management software, decision-support systems, or personal health record systems. For example, the phone may notify the user in advance, via an alarm or vibration, and may also notify a family member, the user's health care provider, electronic-health record decision-support systems or personal health record systems, via a call, email, http, sms text-message, or other form of radiofrequency communication, that the user has an increased likelihood of a near-term future abnormality or fall occurrence. This enables the user or care providers to take preventative measures.

An exemplary operating environment for the present invention is described in connection to FIGS. 1A, 1B and 2, and relates generally to the description of a mobile wearable system for stability-theoretic prediction and prevention of events such as sudden kinematic injury (falling), for use in some embodiments of the invention, and described below in connection to FIGS. 1A, 1B and 2. Referring to the drawings in general, and initially to FIG. 1A in particular, an exemplary operating environment 100 is provided suitable for practicing an embodiment of our invention. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1A, environment 100 includes one or more sensors 116. In one embodiment, sensors 116 include one or more transducers or types of sensors operable for providing electrical signals corresponding to measurements of various conditions, states, of movements of a user. Embodiments of sensor 116 may further include a power supply, processor, memory operable for acquiring and storing user-information and programming instructions, and communication component for communicating the resulting measurements of user-information with brick 130. In some embodiments, the transducer may be a standard electrode, such as a single-terminal electrode, or a specialized multi-segment or noise-reduction electrode.

In some embodiments one or more specialized noise-reduction electrodes may be integrated on a wearable fabric elastomeric band positioned on the user, such as around the user's chest, thereby eliminating or reducing noise, interference, distortion, or artifacts and also improving ease-of-use and patient compliance. In some embodiments sensor 116 includes one or more accelerometeric or gyroscopic transducers operable to determine gyroscopic and accelerometer measurement of angular velocity in at least one of 3 axes (pitch, roll, yaw) and acceleration in at least one of 3 axes (X, Y, Z) and to provide motion signals corresponding to this angular velocity or acceleration. For example, in some embodiments, sensor 116 includes one or more transducers, which can take the form of standard MEMS accelerometer integrated circuit chips, for obtaining electrical kinematic signals from the individual. In one embodiment, a plurality of accelerometer sensors and at least one gyroscope sensor, such as the one manufactured by InvenSense Inc that is used in the Nintendo Wii™ Motion Plus® device, may be deployed on a wearable fabric elastomeric band positioned around the chest. Such an embodiment may be used to eliminate or reduce noise, interference, distortion, or artifacts and improve ease-of-use and patient compliance.

In some embodiments, the processor of sensor 116 is operable to control the frequency of measurements; for example, to read a transducer's output at certain intervals such as 50 times each second; to pre-process or condition the signal, including applying a threshold, noise-filter, or normalizing the raw user-derived signal; read from or store the user-information in memory, and communicate the acquired timeseries of user-information with brick 130 via a communication component of sensor 116. In one embodiment, a floor-threshold is applied such that only movements of a certain magnitude are acquired and communicated to brick 130. For example, it may be desirable in some embodiments not to capture every minuscule motion of the user, but rather only major movements such as stumbles, twists, or sudden jerking motions.

Embodiments of sensor 116 may be designed to measure one or more conditions, states, or movements of a user. For example, in one embodiment sensor 116 obtains electrical signals corresponding to motion of a user and may be worn as a chest-strap, necklace, or a badge on the user's clothing, for example. In another embodiment, sensor 116 obtains electrical cardiac signals of a user and may be worn as a chest-strap, for example. Such a sensor may be designed to measure electrical signals associated with the nerves of the heart or the heart muscle or both. In another embodiment, sensor 116 may include an optical transducer for measuring chemicals in the skin such as keytones, which may be used for determining ketoacidosis of the user. Such an embodiment of sensor 116 may be configured as a skin patch, arm- or leg-band, on the back of a watch, or ankle band, for example. Another embodiment of sensor 116 includes one or more optical sensors for detecting an optical signal across the skin to look at carboxsymmetry, $CO_2$ levels, $O_2$ levels, or a combination of these levels.

In some embodiments, these levels are measured at 10 to 50 times a second thereby resulting in a timeseries of user-information that maybe communicated to brick 130. Other embodiments of sensors 116 include sensors for measuring blood pressure, heart rate, temperature, chemicals such as chemicals in the blood, breath, or on the user's skin, skin or tissue properties, oxygen levels, user motion, movement, or position, or other variables associated with the user's condition, state, or activity. Such sensors are configured to be positioned on or near the user's body in an appropriate manner so that they may function to sense user-data. For example, heart-related sensors may be positioned on or near the chest or at other appropriate locations on the user's body.

In some embodiments, sensor 116 may be worn in contact with user, worn on user's clothes, or located in a user's seat, bed, toilet, or elsewhere in the user's environment, depending on specific type of user-information that the sensor is intended to measure. In one embodiment, sensors 116 include one or more accelerometers, gyroscopic meters, or combination of such devices as to enable one or more sensors 116 to detect user motion, user position or orientation, and sudden changes in user position. In these embodiments the timeseries of user-information communicated to brick 130 may comprise individual motion-events, with each new motion-event adding a member to the timeseries. Thus unlike the timeseries generated by a sensor measuring a physiologic variable 50 times each second, which would have 50 samples each second, the timeseries motion-information is acquired as motions occur, which may not occur at regular intervals. In other words, there could be irregular periods of time between motions that are captured by sensor 116.

In one embodiment, such a sensor 116 may be optimally positioned on the user to measure motion and orientation, such as inline with the user's spine. In one embodiment, the accelerometer and gyroscopic chip-sets built into many smart phones may be used as sensor 116. In such an embodiment, the smart phone, running a program for determining stability-theoretic measures, may monitor user motion-stability and provide to the user and health-care provider early earning warning of a likelihood of increased risk for falling.

In some embodiments, multiple sensors 116 may be employed on or about the user. For example, it may be desirable to have more than one sensor for measuring certain user information such as ketones in the skin, for example, as circulation on certain users varies in the user's body. Additionally, one or more sensors may become compromised, and having multiple sensors provides for robustness. For example a watch sensor may get wet when the user washes his hands and fail to operate as normal, while a second sensor located on the user's ankle may remain effective. In embodiments detection motion of the user, multiple sensors at different locations on the user's body may be employed to obtain more accurate or thorough kinetic information. In such embodiments, motion-signals corresponding to motion in a particular direction or axis or angular motion may be averaged, or may be weighted or scaled according to the location of the sensor. For example, motion signals obtained from a sensor located on the users wrist may be weighted less than motion signals obtained from a sensor worn on the user's chest. In such embodiments, the weighted signals can be combined and used for MdSI determination.

It is also contemplated that multiple sensors of different sensor-types may be utilized to provide a combination of user-information that may more accurately identify a condition or state of the user or increased likelihood of a particular event occurring. For example, a user suffering from the early conditions of a stroke may exhibit multiple signs detectable by different types of sensors 116, such as motion sensors 116, blood-pressure sensors 116, and skin-chemical sensors 116.

Continuing with FIG. 1A, environment 100 includes processing/communication brick 130. Exemplary embodiments of brick 130 are discussed in greater detail in connection to FIG. 1B, but some embodiments of brick 130 include one or more processors operable for processing user-sensor information and determining stability-theoretic measures, a communication module for receiving information from the user-sensors and for communicating results to the user or health-care provider, and a memory for storing received user-information, determined results, and programming instructions. Brick 130 may worn on the user's body, such as clipped to a belt, in a holster, or around the user's neck, or can be carried by the user, such as in the user's pocket or purse, or may be kept with a close enough proximity to the user as to communicate with sensor(s) 116. In some embodiments, sensor(s) 116 are housed within or on brick 130.

In some embodiments, brick 130 is a smart phone running one or more application programs or "apps" for receiving user-sensor information, determining stability-theoretic measures, and communicating results to the user and health care provider. In a smart-phone embodiment, brick 130 uses the phone's communication equipment for communicating user information to a backend, such as a health care provider or decision-support knowledge agent. Brick 130 may use other communication features of the smart phone such as Bluetooth or Wi-Fi to communicate with one or more sensors 116 and in some embodiments, a base station or user computer.

A smart phone may be communicatively-coupled with an additional component for facilitating communication with one or more sensors 116, for processing user-information, or for storing and communicating user results. For example, in one embodiment, brick 130 is communicatively-coupled to a holster or other component containing a communication module for communicating with one or more sensors 116. Such an embodiment is useful where sensors 116 use a communication protocol that is not compatible with brick 130. For example, where sensors communicate using Bluetooth, but brick 130 is embodied on non-Bluetooth enabled smart phone, the user may attach a Bluetooth module to the smart phone to enable it to communicate with sensors 116. Similarly, where sensors 116 communicate using Zigbee or another low-rate wireless personal area network platform, a user may couple a Zigbee-enabled communication module to their smart phone. In another example embodiment, a smart phone may be communicatively-coupled with a base station (not shown) located in the user's house. In one embodiment, the base station could be a personal computer connected to a wireless router or a laptop equipped with RF communication capability such as Wi-Fi or Bluetooth. In one embodiment, the base station communicates with backend 190.

In another embodiment, brick 130 communicates directly with backend 190. Backend 190 includes the health care provider computer system and devices, case-management software, electronic health record decision-support systems and devices, and consumer personal health record systems and devices. In some embodiments, brick 130 stores information on data store 192, which may be local or remotely located, and which may be accessible by backend 190, in some embodiments. In some embodiments, data stores 192 comprises networked storage or distributed storage including storage on servers located in the cloud. Thus, it is contemplated that for some embodiments, the information stored in data store 192 is not stored in the same physical location. For example, in one embodiment, one part of data store 110 includes one or more USB thumb drives or similar portable data storage media. Additionally, information stored in data store 192 can be searched, queried, analyzed via backend 190, such as by a health care provider or by a decision-support knowledge agent, for example.

In some embodiments, sensors 116 communicate with other sensors 116 and with brick 130 over a wired or wireless communication protocol. In one embodiment, sensors 116 communicate using Bluetooth, Wi-Fi, or Zigbee protocols. In some embodiments a low-powered communication protocol is desirable in order to preserve the batter life of the sensor 116. In some embodiments using a communication protocol having a narrow bandwidth, such as Zigbee, sensors 116 may also include a memory buffer for storing user-derived information until it is communicated to brick 130. Sensors 116 may also communicate with other sensors 116 or directly with a base station, in some embodiments.

Figure 1B:
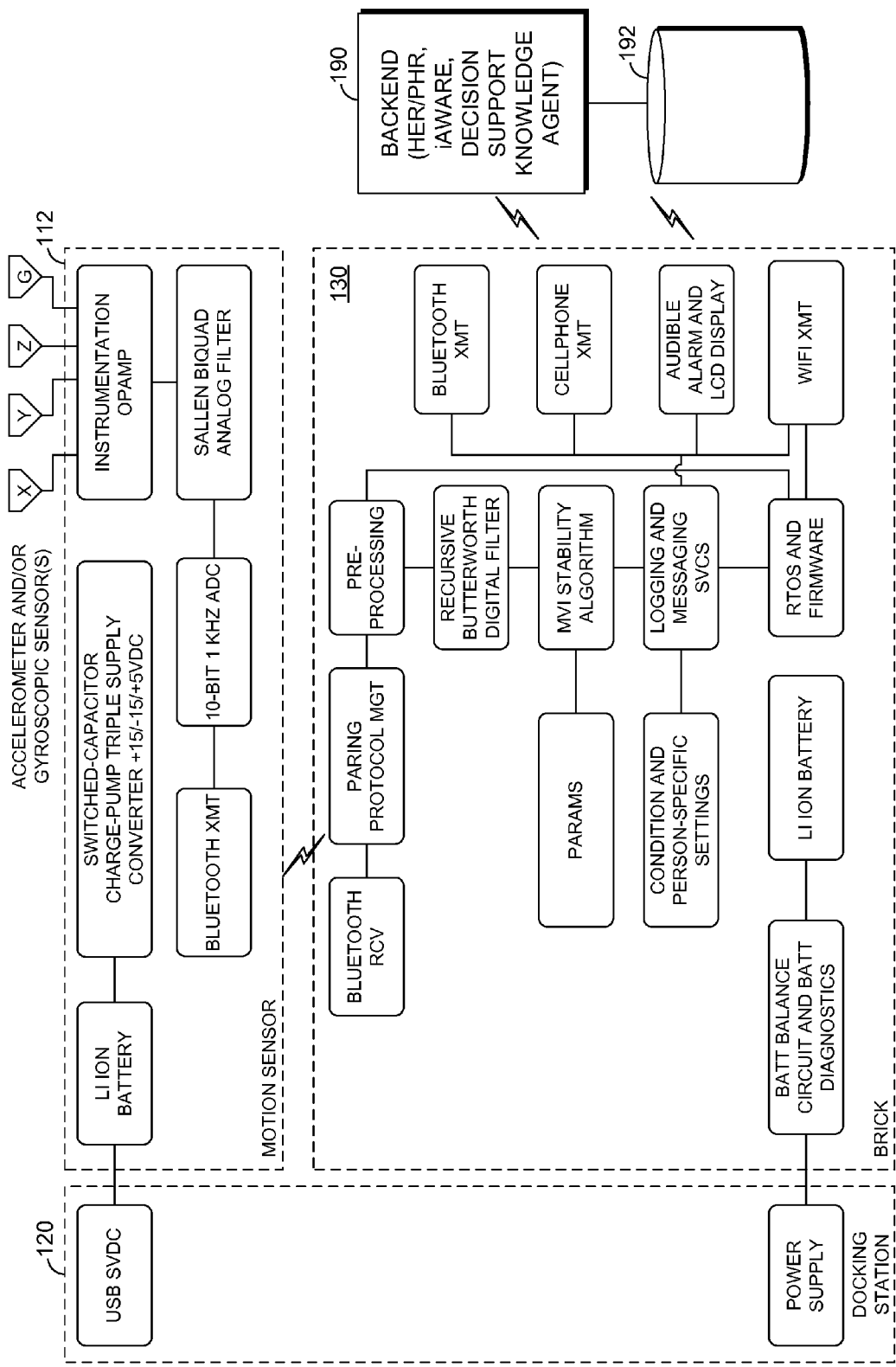
FIG. 1B depicts aspects of an illustrative operating environment suitable for practicing an embodiment of the invention.

Turning now to FIG. 1B, an exemplary operating environment suitable for practicing an embodiment of the invention is shown and referenced generally as 150. As shown in FIG. 1B, brick 130 is communicatively coupled to wearable motion sensor 112, which is one embodiment of sensor 116, and docking station 120. In the embodiment shown in FIG. 1B, docking station 120 recharges a battery in brick 130 and in chest-strap sensor 112. Brick 130 is also communicatively coupled to backend 190, and data store 192, which are described previously in connection to FIG. 1A.

The embodiment illustratively depicted in FIG. 1B, may be used for generating a Lyapunov exponent classifier and verifying and validating whether such a detector achieves statistical sensitivity and specificity in the intended mortality range of deployment, sufficient for satisfactory performance in the use for classifying patients according to in-hospital mortality outcome.

In the embodiment shown in FIG. 1B, motion sensor 112 includes one or more accelerometers or gyroscopic transducers. In this embodiment, the transducers are coupled to an instrumentation operational amplifier, an analog filter, an analog-to-digital converter, and a Bluetooth or similar RF communication component, thereby enabling motion sensor 112, when positioned on the user, to obtain raw motion signals of the user, capture and digitize the raw motion signals, and communicate this information to brick 130. Motion sensor 112 also includes a power supply made up of a battery and multiple-output supply converter.

In the embodiment shown in FIG. 1B, brick 130 includes a Bluetooth or similar RF communication component operable to receive user-information from motion sensor 112 or from other sensors 116, preprocessing and filtering components operable to condition and format the received user information for the movement variability index (MVI) stability processing, and a processor for determining MdSI, which is described in connection to FIGS. 3 and 4, below. Embodiments of brick 130 may also include a Bluetooth, cell-phone, or Wi-Fi communication component for communicating results ultimately to backend 190 and data store 192, and an alarm and display for providing results, diagnostic feedback, power levels, and other information to a user or for receiving inputs from a user such as parameters and device settings. Embodiments of brick 130 may also include memory for storing parameters, settings, firmware and programming instructions, and determined results. Embodiments of brick 130 may also include a power supply which in one embodiment comprises a battery and a battery balance circuit. In one embodiment, brick 130 is a computer system with one or more processors, memory, and input/output functionality.

In one embodiment, brick 130 is a computer system comprising the following hardware and firmware components: a 32-bit 48 MHz AT91SAM7S256 (ARM7TDMI) main microprocessor with 256 KB flash memory and 64 KB RAM, an 8-bit 4 MHz ATmega48 microcontroller with 4 KB flash memory and 512 Bytes RAM, a 26 MHz CSR BlueCore 4 Bluetooth controller with 1 MB flash memory and 47 KB RAM, and 100×64 pixel LCD matrix display. In one embodiment, motion-signal pre-processing, recursive IIR low-pass Bessel filter, and MdSI calculation software algorithms were implemented in a dialect of the C language (NXC) using the BricxCC compiler and version 1.28 firmware for the ARM7 processor. It should be understood that variations in hardware and firmware are contemplated by and within the scope of the invention, and are provide here for illustrative purposes.

Figure 2:
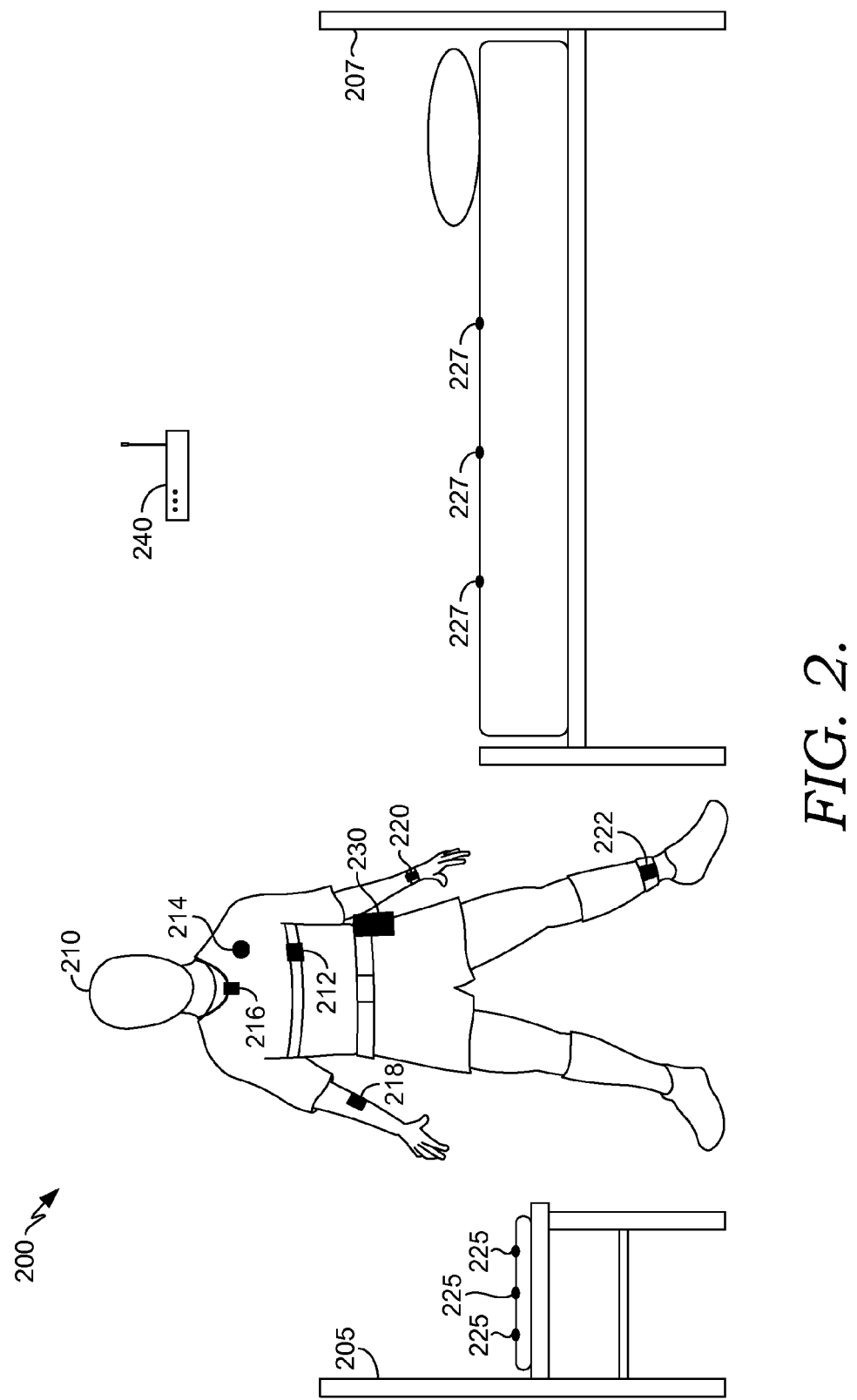
FIG. 2 depicts aspects of an illustrative operating environment suitable for practicing an embodiment of the invention.

FIG. 2 illustratively depicts aspects of an illustrative operating environment suitable for practicing embodiments of the invention and is referenced generally as 200. Environment 200 depicts a user 210 wearing various example types of sensors 116, including: chest-strap sensor 212, badge-sensor 214, which may be attached to a user's clothing or integrated into a user's clothing, necklace sensor 216, skin-patch sensor 218, watch-strap sensor 220, and ankle or leg sensor 222. User 210 is also wearing a brick 230 at the user's waist. Also depicted in environment 200 is a chair 205 having sensors 116 integrated into a seat cushion, shown as sensors 225, and a bed 207 having sensors 116 integrated into the bed shown as sensors 227. In some embodiments, environment 200 includes a base station 240, which may be communicatively coupled to brick 230 or one or more sensors 116. As further described in connection to FIG. 1A, in some embodiments, a base station, such as base station 240, is communicatively coupled to a user's computer, to a backend 190, or to data store 192.

Figure 5:
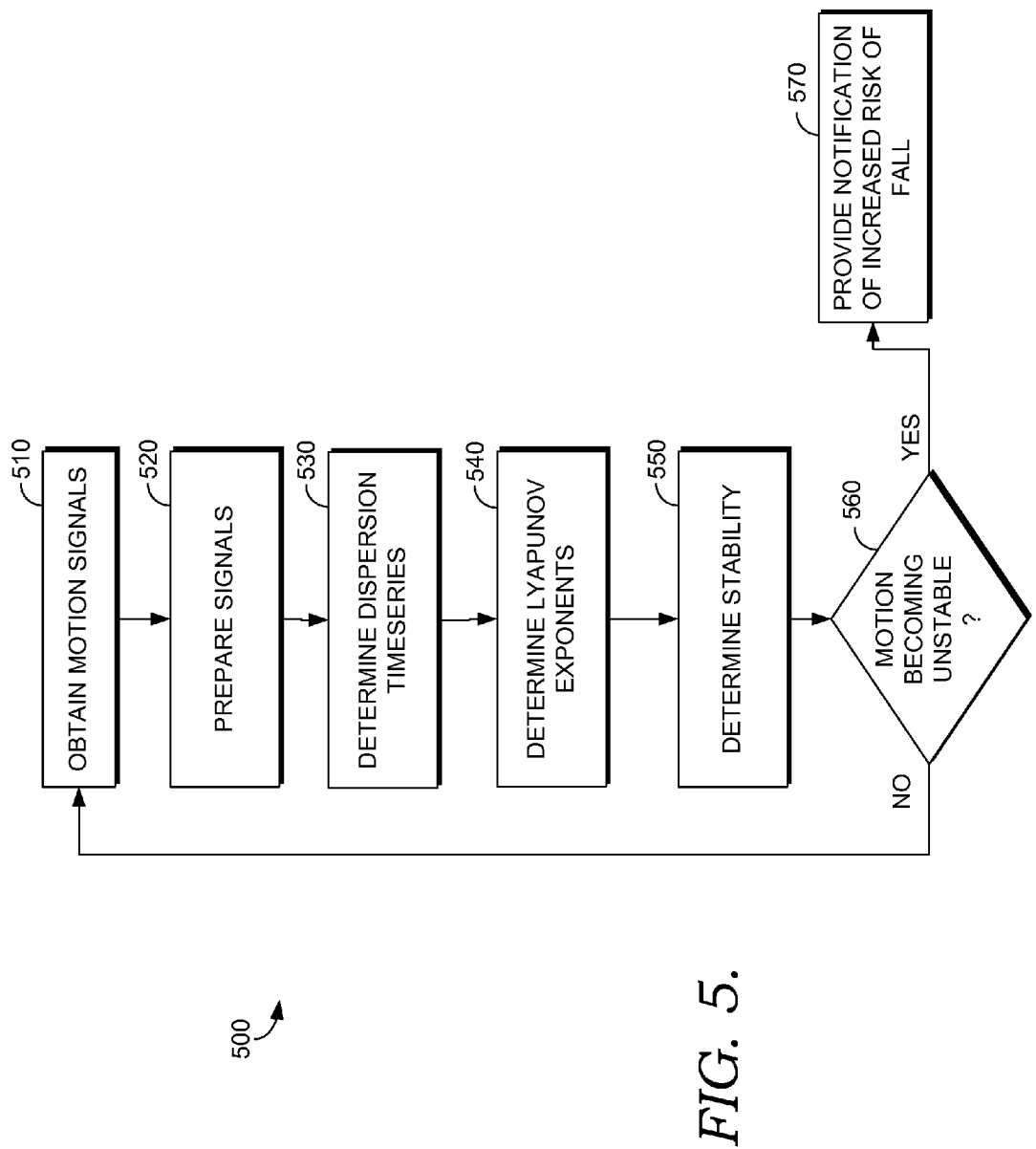
FIG. 5 depicts a flow diagram of an exemplary method for determining a motion dispersion stability index for an individual, in accordance with embodiments of the invention.

Turning now to FIG. 5, a flow diagram 500 is provided illustrating an exemplary method according to one embodiment. At a high level, flow diagram 500 illustratively depicts a method for determining a motion dispersion stability index (MdSI) for an individual. The MdSI is determined by applying an objective function to user-derived information such as motion-signal information obtained from one or more sensors 116. Some embodiments of the invention process the information in serial acceleration and rotational velocity measurements associated with the individual's movements and to calculate MdSI(t) timeseries, where t represents time, as a function of the individual's instantaneous MdSI determinations. As shown in flow diagram 500, a logistic regression equation and algorithm based on Lyapunov stability measures of motion dispersion as a continuous or discrete function of time is utilized. A Lyapunov exponent (of MdSI(t) or any other timeseries signal) is a quantitative measure of separation of trajectories that diverge widely from their initial positions and is related to how chaotic a system is. The larger the exponent, the more chaotic the system. For periodic signals, the Lyapunov exponent is zero. A random but stable signal will also have an exponent very close to zero.

In another embodiment, a decision tree algorithm may be used to evaluate the classification ability of several methods of measuring motion dispersion. In yet another embodiment, a support vector machine (SVM) algorithm utilizing timeseries of calculated motion variables including width of root-mean-square (RMS) motion dispersion is applied to generate a prediction of falling risk. Still in yet another embodiment, a combination of a Lyapunov-based algorithm, a descision tree algorithm, or a support vector machine may be employed.

At a step 510, motion signals of a user are obtained using one or more sensors 116. User-information representative of the motion signals is communicated from one or more sensors 116 to brick 130. In one embodiment, sensor 116 captures motion waveforms corresponding to the user's movement, thereby resulting in a timeseries of motion-signal intervals. It will be understood by those skilled in the art that in some embodiments, other waveform measures or physiologic timeseries may be used without departing from the scope of the invention. For example, in some embodiments timeseries variables relating to heart, respiratory, glucometry, accelerometry, oximetry, capnometry, plethysmography (perfusion), or other physiologic variables may be used.

In steps 520 through 550, the motion dispersion stability index (MdSI) as a function of the continuous or discrete kinematic timeseries is calculated. In some embodiments, any ectopic beats and the sinus beats immediately preceding and following the ectopic beats are first eliminated, as part of a step 520 before calculating the maximal value of root-mean-square differences. Low-pass filtering may be performed to remove baseline drift from the electrical signal, in some embodiments. Normalizing the maximal value of root-mean-square differences to the absolute magnitude of the signal-averaged motions may also be performed, in some embodiments, before calculating and updating the MdSI(t) timeseries. Instructions carried on a computer-readable storage medium (e.g., for identifying QT intervals and calculating MdSI(t)) can be implemented in a high level procedural or object oriented programming language to communicate with a computer system, in one embodiment. Alternatively in another embodiment, such instructions can be implemented in assembly or machine language. The language further can be compiled or interpreted language, in one embodiment.

It is further contemplated that in some embodiments, the MdSI-related processing occurring in steps 520 through 540 occurs in realtime or near realtime, simultaneously, as electrical kinematic signal-information is collected in step 510, thereby allowing a skilled operator to monitor an individual's MdSI during pharmacologic or exercise physiologic stress, if desired. More generally, in some embodiments, processing steps 520 through 550 are performed substantially simultaneously with the step 510 of collecting the kinematic signals in near real-time, so as to enable the ambulatory consumer to go about their daily activities and receive smartphone or other mobile alert messages from brick 130 device in case any elevated-risk conditions are detected.

At step 520, the collected kinematic signals are prepared. In some embodiments this preparation includes pre-processing or signal conditioning. Step 520 may be performed by sensor 116, by brick 130, or a combination. In embodiments, thresholding, artifact censoring, normalizing, noise filtering, or other DSP filtering, or any combination of these, may be applied to the raw signal information. In one embodiment a floor threshold is applied by zeroing out the motion signals unless the amplitude, in the X, Y, Z axis, angular (gyro) or a sum of these, exceeds a certain minimum value. In some embodiment, the amplitudes of one or more acquired signals, representing motions about the X,Y, and Z axis, and angular (gyro) motions, are summed together resulting in a motion signal where amplitude corresponds to motion in any of the one or more X, Y, and Z axis, or angular motions used in the summation. Furthermore, in some embodiments, the motion-signal that corresponds to a motion along a particular axis or angular motion may be weighted or scaled prior to the summation. For example, it may be desirable to emphasize z-axis or angular motions (or both) by assigning a higher weight to the amplitudes of signals corresponding to z-axis motions or angular motions. Thus, in such embodiments, a user's movement along the x and y axes (usually horizontal) would be less significant for the MdSI determination than movement along the z-axis (usually vertical) or angular movement (such as twisting and turning).

In some instances, inconsistencies in accelerometry measurements may occur in part because of skeletal muscle signal artifact, patient position, time of day, or misplaced sensors. Moreover, failure to adjust for sensor drift can also skew an analysis. Accordingly, in some embodiments integrals of acceleration and angular velocity are taken into account and stability measurements that are generated shortly after any fall or impact are ignored.

At steps 530, 540, and 550, MdSI timeseries is determined, Lyapunov exponents are calculated, and used to determine stability of the monitored condition of the user. By way of example and not limitation, the methodology of the invention may be understood through the following steps: Let $L(x_1, x_2, \ldots, x_n)$ be a scalar function of n components of x, where the n components (sampled timeseries values of the linear combination of one or more accelerometer-axis outputs, such as a 3-axis accelerometer output, and 1-axis gyro output) comprise the vector $x=\{x_1, \ldots, x_n\}$. $L(x)$ is positive-definite in a neighborhood N of the origin if $L(x)>0$ for all $x \neq 0$ in N and $L(0)=0$. Let $x^*(t)=0$, $t \geq t_0$ be the zero solution of the homogeneous system $x\phi=Ax$ where $x(0)=x_0=0$. Then $x^*(t)$ is globally stable for $t \geq t_0$ if there exists $L(x)$ with the following properties in some neighborhood N of 0: (i) $L(x)$ and its partial derivatives are continuous; (ii) $L(x)$ is positive-definite, or $L(x)>0$; and (iii) $dL(x)/dt$ is negative-definite, or $dL(x)/dt<0$.

By (ii) the quadratic form $L(x)$ exhibits an ellipsoid curve. By (iii), the ellipsoid curve shrinks to zero. Choose $\epsilon>0$ such that $N\epsilon \subset N$ above. Any half-path starting in $N\epsilon$ remains in it because $L(x)$ is a quadratic form (by (ii)) which exhibits an ellipsoid curve that is continuous as well as its partial derivatives (by (i)). The same holds for every sufficiently small $\epsilon>0$ and hence for every sufficiently small neighborhood of the origin. The zero solution is therefore globally stable.

In other words, the system $(dx/dt)=Ax$ is globally stable if and only if for some positive-definite matrix W, the equation: $A^tH+HA=-W$ has a positive-definite matrix H. If for some positive-definite matrix W, the equation $A^tH+HA=-W$ has a positive-definite matrix H, let us show that $(dx/dt)=Ax$ is globally stable. Since H is positive-definite, then $L(x)=x^tHx$ is positive-definite (where $x^t$ is now the transpose of x and not the time derivative), i.e. $L(x)>0$. Also, $L(x)$ positive-definite implies that $V(x)$ and its partial derivatives are continuous. Differentiating $L(x)$, then: $dL(x)/dt=(dx^t/dt)Hx+x^tH(dx/dt)$ or, as $dx/dt=Ax$: $dL(x)/dt=(Ax)^tHx+x^tHAx=x^tA^tHx+x^tHAx=x^t(A^tH+HA)x$. Thus, as $A^tH+HA=-W$: $dL(x)/dt=x^t(-W)x$. W determined to be positive-definite implies that $-W$ is negative-definite, thus: $dL(x)/dt=x^t(-W)x<0$.

Finally, it is notable that (i) $L(x)$ and its partial derivatives are continuous; (ii) $V(x)$ is positive-definite; (iii) $dL(x)/dt$ is negative-definite. As a result, $dx/dt$ is globally stable according to our previous theorem. Conversely, if $dx/dt=Ax$ is stable, then for some positive-definite matrix W, the equation $A^tH+HA=-W$ has a positive-definite matrix H. $dx/dt=Ax$ stable implies all the eigenvalues of A are negative, i.e. $\lambda<0$ for any eigenvalue $\lambda$ of A. Now, as $\lambda x=Ax$, then $(Ax)^t=(\lambda x)^t$, which implies $x^tA^t=\lambda x^t$. Thus, premultiplying $A^tH+AH$ by $x^t$ and post-multiplying it by x, the following is obtained: $x^t(A^tH+HA)x=x^t(-W)x$; or: $x^tA^tHx+x^tHAx=x^t(-W)x$; or substituting in $\lambda x^t$ and $\lambda x$: $\lambda x^tHx+x^tH\lambda x=x^t(-W)x$; or simply: $2\lambda x^tHx=x^t(-W)x$. As $-W$ is negative-definite, then $x^t(-W)x<0$, thus $2\lambda x^tHx<0$. As $\lambda<0$ by the assumption of stability, then it must be that $x^tHx>0$, or H is a positive-definite matrix. Accordingly, a real n×n matrix A is a stable matrix if and only if there exists a symmetric positive-definite matrix H such that $A^tH+HA$ is negative-definite. In one embodiment, a choice of W=I may be made and H can be solved and solve for H in the equation $A^tH+HA=-I$. The solution has the form $H=\alpha(A^t)^{-1}A^{-1}+\beta 1$ where $\alpha$ and $\beta$ are constants. Thus, choosing a Lyapunov function, $L(x)=x^tHx$, this solution is used to determine H. The Lyapunov function or thread may be executed continuously, under a real-time operating system (RTOS), in some embodiments, enabling parameters and timeseries information to be passed to the Lyapunov function or thread in near realtime.

Furthermore, in some embodiments, a second-order polynomial function $f(x)=r*x*(1-x)$ is utilized to represent a system whose stability may be characterized by the invention. In one embodiment, the system may be characterized by a function of different order or form. If the structure of a particular system is not known, the structure may be developed by Taylor series regression, spectral analysis or timeseries analysis techniques or other methods of modeling known to those of skill in the art.

At a step 530 a dispersion time series is calculated. In one embodiment, a standard deviation (SD) of the amplitude is calculated on an M-wide time series array, such as, for example, $SD\{A_1, \ldots, A_{N-M}\}$, $SD\{A_2, \ldots, A_{N-M+1}\}$, $\ldots$, $SD\{A_{M+1}, \ldots, A_N\}$, where A represents amplitude, and each member of the timeseries corresponds to a motion event, such as movement in either the X,Y or Z-axis direction, rotational movement, or a combination of these. For example, in one embodiment, each member of the time series represents a linear combination of 3-axis accelerometer outputs plus 1-axis gyro output. In one embodiment M may vary between 1000 to 300 samples; with accuracy generally increasing as the size of M increases.

At a step 540, Lyapunov exponents are calculated for each member of the time series, thus: $SD\{A_1, \ldots, A_{N-M}\} \rightarrow \lambda_1$, $SD\{A_2, \ldots, A_{N-M+1}\} \rightarrow \lambda_2$, $\ldots$, $SD\{A_{M+1}, \ldots, A_N\} \rightarrow \lambda_{M+1}$. Accordingly, in some embodiments each member of the time series of standard deviations of the linear combination of 3-axis accelerometer outputs plus 1-axis gyro output represents an MVI value. At a step 550, stability is assessed based on the determined values of the Lyapunov exponents. In some embodiments $\lambda_i>0$ implies an unstable process. In some embodiments, a threshold TH may be applied. For example, for instability to be present, $\lambda_i>TH$, which can account for minor fluctuations that may occur in the user, such as fluctuations that may arise when a user's activity level changes. In other embodiments, such as in the example discussed later on, the difference between $\lambda_i$ and a reference value is determined, and instability is present where this difference exceeds a certain threshold.

At a step 560 it is determined whether the user's motion is showing signs of instability, based on the results of step 550. In one embodiment, if the stability is present, then the process returns to step 510 and additional motion signals or other physiologic timeseries information is obtained from one or more sensors 116. In one embodiment, new kinematic-signal information or other physiologic timeseries information continuously collected as it is available simultaneously as processing for determining stability-theoretic measures occurs. In one embodiment, the Lyapunov exponents are calculated on a sliding boxcar array that is M-samples wide, with new Lyapunov exponents calculated each W samples. In embodiments where W equals 1 motion event, then new Lyapunov exonents are calculated on the M-wide timeseries array for each new motion event. In some embodiments, W may represent several samples. If at step 560, the results of step 550 indicate the presence of instability, then the method proceeds to step 570. At a step 570, a user, health care provider, or decision support system is notified that the user is becoming unstable. In one embodiment, this instability indicates that the user is facing an increased likelihood of falling. In one embodiment, this instability indicates a change in the patient's condition, which may be for the better or worse. In one embodiment, the user may be notified via brick 130 in the form of a text message, audible alarm or vibration. In one embodiment, the health care provider maybe notified via brick 130 in the form of a text message, call, or other appropriate form of communication. In one embodiment, a visual or graphical display of the electrical signals or a numerical or digitized representation of the monitored motion variables and stability indices may be presented on brick 130, a user's computer communicatively coupled to brick 130, or a health care provider's computer communicatively coupled to back-end 190. For example, in one embodiment, an audible alert sounds or a vibration is emitted upon detection of patterns and MdSI values indicative of actionable increased risk of falling. In one embodiment, a radiofrequency message may be emitted to security-/confidentiality-controlled, mated transceivers such as BlueTooth smartphones, Wi-Fi connections with personal computers or electronic medical records systems, and similar devices.

Figure 3:
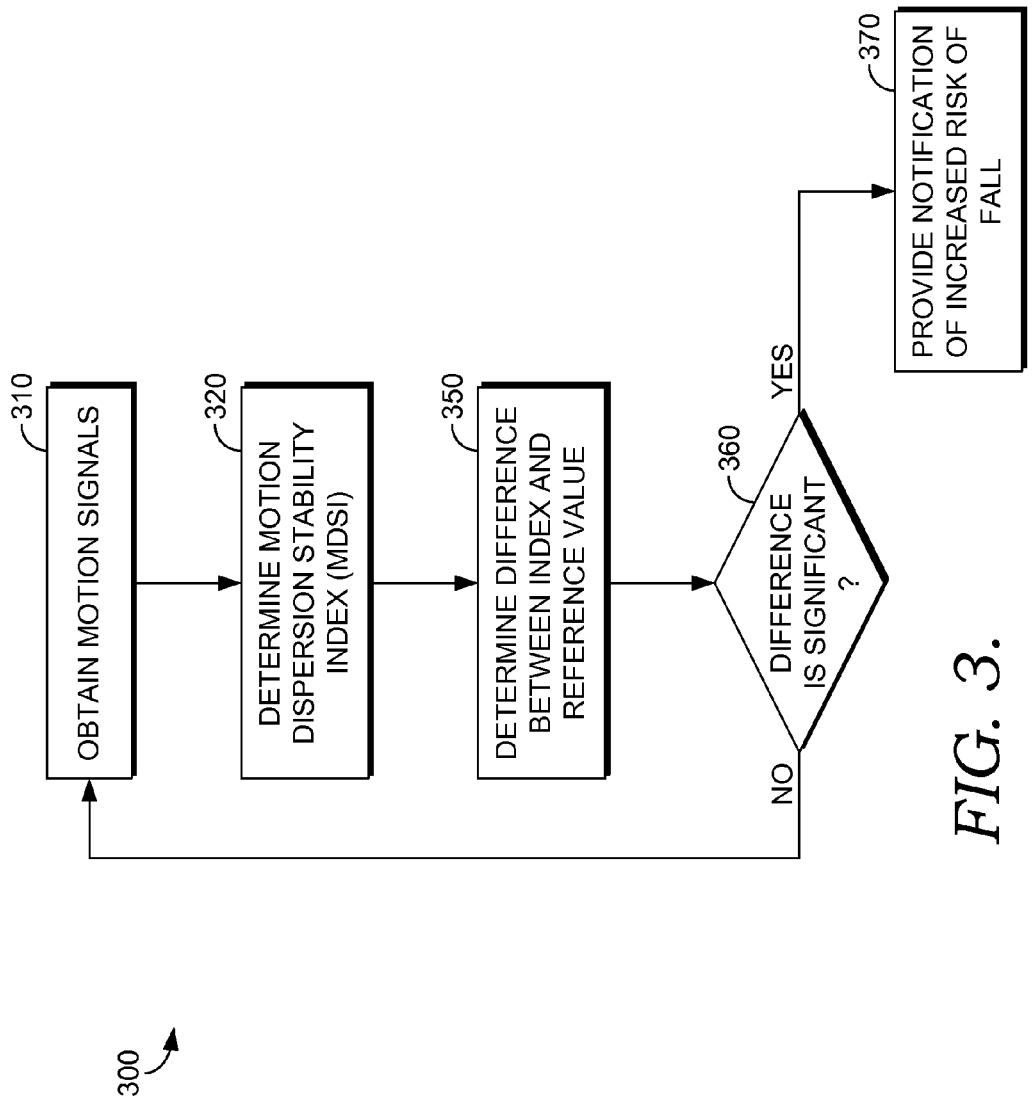
FIG. 3 depicts a flow diagram of an exemplary method for automatically predicting ventricular arrhythmias in an individual that are likely to result in sudden kinematic death, in accordance with embodiments of the invention.

Turning to FIG. 3 a flow diagram 300 is provided illustrating an exemplary method according to one embodiment. At a high level, flow diagram 300 illustratively depicts a method for determining a motion dispersion stability index (MdSI) for an individual. The MdSI is determined by applying an objective function to user-derived information such as kinematic signal information obtained from one or more sensors 116. The method also includes determining the difference between the stability index value and a reference value to detect presence of instability of motion dispersion or other measurements. It has been determined, as further described below in connection to that a significant difference between the two values indicates an increased risk of falling for an individual. In one embodiment, the reference value is selected based on other parameters associated with the user.

At a step 310, motion signals of a user are obtained using one or more sensors 116. User-information representative of the motion signals is communicated from one or more sensors 116 to brick 130. In some embodiments, pre-processing and conditioning of the motion signal information, which may include, for example, thresholding or flooring, artifact censoring, normalization, or DSP filtering, and other pre-processing and conditioning as described in connection with step 520 in FIG. 5, takes place either at the sensor 116 in brick 130, or both. At a step 320, MdSI is determined in accordance with the method described in connection to steps 520 to 550 of FIG. 5. At a step 350, the difference between the motion dispersion stability index and a reference value is determined. Based on the results of this difference, at a step 360, a determination is made as to whether the difference is significant.

In one embodiment, significance is based on parameters associated with the particular user. For example, a younger more active user may be afforded a greater difference than a less active user who has a known history of falling, stumbling, other motor problems, or otherwise has a higher risk for falling. At step 360, where the determined difference is not significant, the method returns to step 310. In one embodiment, new kinematic information or other physiologic timeseries information is continuously collected as it is available simultaneously as processing for determining stability-theoretic measures occurs, as described above in connection to FIG. 5. At step 360, where the determined difference is significant, the method proceeds to a step 370. At step 370, notification of increased risk for falling is provided. In one embodiment, the notification is provided in a manner as described at step 570 in connection to FIG. 5.

Figure 4:
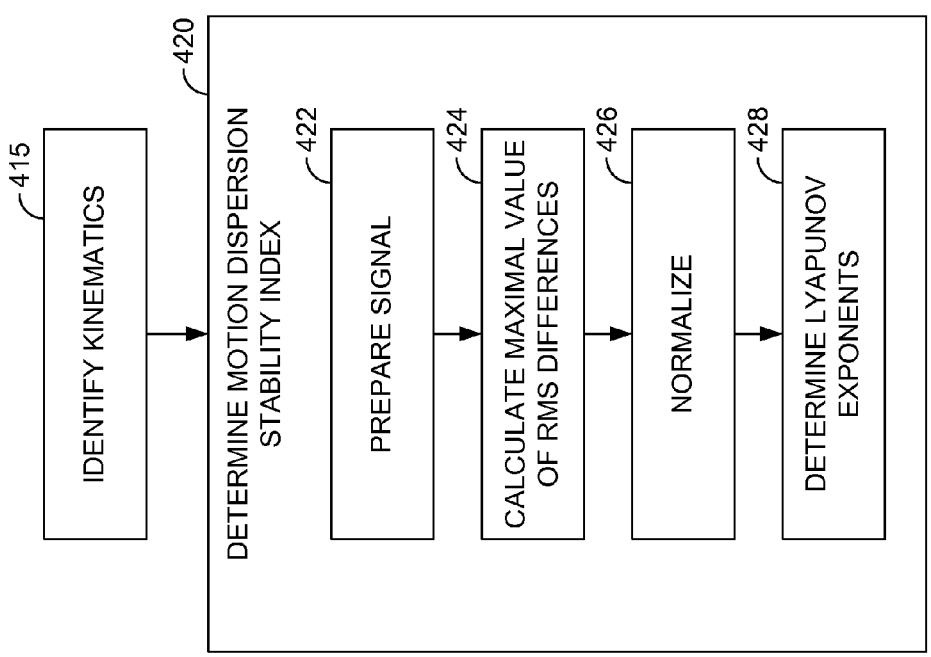
FIG. 4 depicts a flow diagram of an exemplary method for determining a motion dispersion stability index for an individual, in accordance with embodiments of the invention.

Turning now to FIG. 4, a flow diagram 400 is provided illustrating an exemplary method according to one embodiment. At a high level, flow diagram 400 illustratively depicts a method for determining a motion dispersion stability index (MdSI) for an individual. At a step 415, translational or rotational kinematic information is determined from accelerometer or gyroscopic signals representative of movements of an individual. At a step 420 the MdSI is computed, in accordance with the method described in connection to steps 520 to 550 of FIG. 5, as a function of the kinematics determined in step 415. In the embodiment shown in FIG. 4, at a step 422, the user-derived signal is prepared. In some embodiments, this includes pre-processing and conditioning of the motion signal information, which may include, for example, thresholding, artifact censoring, normalization, or DSP filtering, as described in connection with step 520 in FIG. 5. Such pre-processing may be performed by sensor 116, brick 130, or both, in some embodiments. At a step 424, the maximal value of root-mean-square differences is determined. At a step 426, the maximal value of root-mean-square differences are normalized to the absolute magnitude of the signal-averaged motions. At a step 428, the Lyapunov exponents are determined, in accordance with the method described above in connection to FIG. 5.

By way of example using the embodiment of FIG. 1B, twelve subjects between the ages of 75 and 92 and 14 control subjects with no known risk factors for falling were studied. There were 11 falling events in this cohort. The control subjects were free of known cardiovascular disease except for mild hypertension in one subject.

Using the embodiment of FIG. 1B, the MdSI accurately predicted falling as shown in Table 1 below, where $P<0.005$ Fisher Exact Test, two-tailed.

TABLE 1

|  | Falling | No Falling |
| --- | --- | --- |
| MdSI positive | 9 | 1 |
| MdSI negative | 2 | 14 |

In this initial study connected with the reduction-to-practice of the present invention, the sensitivity of the MdSI metric to predict falling was 83% and the specificity was 93%. The odds-ratio was 63 and the number-needed-to-treat (NNT) was 2.

Additionally, a small sample size of cases and controls was available, so risk stratification by neurologic diagnosis or other patient-grouping variables was not evaluated, here. In that regard, it is important to identify those patients at high risk for falling but who do not have symptoms or prior history of falling. In follow-on studies, it is anticipated that specific submodels to predict falling in the presence of those covariables will be developed. Secondly, it should be noted that falling is not always because of cerebellar or vestibular causes. For example, muscle weakness or cognitive failures may be a more frequent cause of falling in the elderly. It is thus anticipated that stability-theoretic prediction models as set forth in the present invention should be useful in these circumstances. Thirdly, the cases and controls available to us were from acute-care medical-surgical hospital-based settings.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. Computer-readable media having computer-executable instructions embodied thereon that when executed, facilitate a method for automatically predicting life-threatening ventricular arrhythmias that are likely to result in sudden kinematic death (falling) in humans, the method comprising:
   obtaining motion signals representative of motion of an individual;
   detecting the presence of instability (chaos or trajectory-divergence) of motion dispersion or other measurements in said signals;
   determining, utilizing an objective function, a motion dispersion stability index (MdSI) from said signals based on one or a plurality of previous time intervals; and
   determining a difference between the index and a reference value to classify the likelihood of events leading to falling within a future time interval,
   wherein a significant difference is indicative of an increased risk for falling.

2. The computer-readable media of claim 1, wherein the objective function evaluates digitized kinematic waveforms from the one or a plurality of previous time intervals to classify the likelihood of a cascade of events leading to falling within a future time interval.

3. The computer-readable media of claim 1, wherein the objective function comprises a timeseries calculated from serially-acquired waveform data embodying the Lyapunov exponent.

4. The computer-readable media of claim 3, wherein the results of the objective function are used by a decision-support algorithm to determine a quantitative risk for falling.

5. The computer-readable media of claim 4, wherein the decision-support algorithm comprises at least one of a decision-tree, a suite of 'if-then' production rules and an inference engine, a support vector machine (SVM), a logistic regression equation, an automated neural network, or a statistical predictive algorithm.

6. Computer-readable media having computer-executable instructions embodied thereon that when executed, facilitate a method for determining a motion dispersion stability index for an individual, the method comprising:
   identifying translational or rotational kinematics from accelerometer or gyroscopic signals representative of movements of an individual; and
   determining a motion dispersion stability index based on the kinematics from one or a plurality of previous time intervals, for determining a likelihood of falling within a future time interval.

7. The computer-readable media of claim 6, wherein said determining a motion dispersion stability index based on the kinematics further comprises eliminating anomalous kinematic values following fall occurrences.

8. The computer-readable media of claim 7, wherein said fall occurrences comprise a predominantly translational motion or a predominantly rotational motion.

9. The computer-readable media of claim 7, wherein the method further comprises filtering the signal prior to determining the motion dispersion stability index.

10. The computer-readable media of claim 7, wherein said determining a motion dispersion stability index based on the kinematics further comprises removing baseline fluctuation from said signal prior to determining the motion dispersion stability index.

11. The computer-readable media of claim 7, wherein said determining a motion dispersion stability index based on the kinematics further comprises:
   calculating the maximal value of root-mean-square differences; and
   normalizing the maximal value of root-mean-square differences to an absolute magnitude of signal-averaged motions.

12. The computer-readable media of claim 7, wherein said determining a motion dispersion stability index based on the kinematics further comprises calculating and storing Lyapunov exponents.

13. A method for automatically predicting sudden kinematic injury (falling) in humans the method comprising:
   obtaining motion signals representative of motion of an individual;
   determining, utilizing an objective function, a motion dispersion stability index (MdSI) from said signals based on one or a plurality of previous time intervals, to classify a likelihood of events leading to falling within a future time interval; and
   determining a difference between the index and a reference value,
   wherein a significant difference is indicative of an increased risk for falling.

14. The method of claim 13, wherein the objective function evaluates digitized kinematic waveforms from the one or a plurality of previous time intervals to classify the likelihood of a cascade of events leading to falling within a future time interval.

15. The method of claim 13, wherein the objective function comprises a timeseries calculated from serially-acquired waveform data embodying a Lyapunov exponent of one or a plurality of kinematic or other physiologic variables as functions of time.

16. The method of claim 13, wherein the results of the objective function are used by a decision-support algorithm to determine a quantitative risk for falling.

17. The method of claim 16, wherein the decision-support algorithm comprises at least one of a decision-tree, a suite of 'if-then' production rules and an inference engine, a support vector machine (SVM), a logistic regression equation, an automated neural network, or a statistical predictive algorithm.

18. The method of claim 13, wherein the method further comprises providing a notification to a health care provider when said increased risk for falling is indicated.

19. The method of claim 13, wherein the reference value is determined based on parameters associated with the individual including at least one of age, mobility, and falling history; wherein the determined difference is determined as significant when the difference exceeds a threshold; and wherein the threshold is based on a value indicative of minor fluctuations in activity level of the individual.

20. The computer-readable media of claim 1, wherein the reference value is determined based on parameters associated with the individual including at least one of age, mobility, and falling history; wherein the determined difference is determined as significant when the difference exceeds a threshold; and wherein the threshold is based on a value indicative of minor fluctuations in activity level of the individual.

* * * * *